(12) United States Patent
Greenberg et al.

(10) Patent No.: US 10,549,096 B2
(45) Date of Patent: *Feb. 4, 2020

(54) AGGREGATE ELECTRODE FOR NEURAL STIMULATION

(71) Applicant: SECOND SIGHT MEDICAL PRODUCTS, INC., Sylmar, CA (US)

(72) Inventors: Robert J. Greenberg, Los Angeles, CA (US); Neil H. Talbot, La Crescenta, CA (US); Proyag Datta, Castaic, CA (US); Dustin Tobey, Glendora, CA (US); David Daomin Zhou, Saugus, CA (US); Jessy Dorn, Los Angeles, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/845,000

(22) Filed: Dec. 18, 2017

(65) Prior Publication Data

US 2018/0104487 A1    Apr. 19, 2018

Related U.S. Application Data

(63) Continuation of application No. 15/154,757, filed on May 13, 2016, now Pat. No. 9,861,820.

(60) Provisional application No. 62/161,134, filed on May 13, 2015.

(51) Int. Cl.
| | | |
|---|---|---|
| *A61N 1/36* | (2006.01) | |
| *A61N 1/05* | (2006.01) | |
| *A61B 5/04* | (2006.01) | |
| *A61N 1/375* | (2006.01) | |
| *A61N 1/372* | (2006.01) | |

(52) U.S. Cl.
CPC ...... *A61N 1/36046* (2013.01); *A61B 5/04001* (2013.01); *A61N 1/0531* (2013.01); *A61N 1/3606* (2013.01); *A61N 1/3758* (2013.01); *A61N 1/36135* (2013.01); *A61N 1/37217* (2013.01)

(58) Field of Classification Search
CPC ... A61F 9/08; A61F 2/147; A61F 2/14; A61N 1/36; A61N 1/0543; A61N 1/36046; A61N 1/05
USPC .......................................................... 607/54
See application file for complete search history.

(56) References Cited

U.S. PATENT DOCUMENTS

| | | | |
|---|---|---|---|
| 5,109,844 | A | 5/1992 | de Juan, Jr. et al. |
| 5,935,155 | A | 8/1999 | Humayan et al. |
| 59,447,347 | | 8/1999 | Greenberg et al. |
| 6,400,989 | B1 | 6/2002 | Eckmiller |
| 6,458,157 | B1 | 10/2002 | Suaning |
| 6,718,209 | B2 | 4/2004 | Williamson et al. |
| 6,974,533 | B2 | 12/2005 | Zhou |
| 9,861,820 | B2 * | 1/2018 | Greenberg ......... A61N 1/36046 |
| 2002/0095080 | A1 * | 7/2002 | Cory ................. A61B 5/04001 |
| | | | 600/393 |

(Continued)

*Primary Examiner* — Carl H Layno
*Assistant Examiner* — Jon Eric C Morales
(74) *Attorney, Agent, or Firm* — Scott Dunbar

(57) ABSTRACT

The present invention is a flexible circuit electrode array for neural stimulation including a polymer base layer, a metal trace layer on the polymer base layer, and a polymer top layer on the metal traces layer, where the metal trace layer forms at least one electrode made of multiple smaller common electrodes connected by electrical traces.

13 Claims, 16 Drawing Sheets

(56) References Cited

U.S. PATENT DOCUMENTS

| | | |
|---|---|---|
| 2005/0201585 A1 | 9/2005 | Jannard et al. |
| 2005/0222624 A1 | 10/2005 | Greenberg et al. |
| 2006/0129207 A1 | 6/2006 | Fried et al. |
| 2009/0216295 A1* | 8/2009 | Zrenner ............... A61N 1/0543 607/54 |
| 2012/0277834 A1* | 11/2012 | Mercanzini ........ A61B 5/04001 607/62 |
| 2013/0319972 A1* | 12/2013 | Greenberg ........... A61N 1/0543 216/17 |
| 2015/0157862 A1* | 6/2015 | Greenberg ........... A61B 5/6868 607/60 |

* cited by examiner

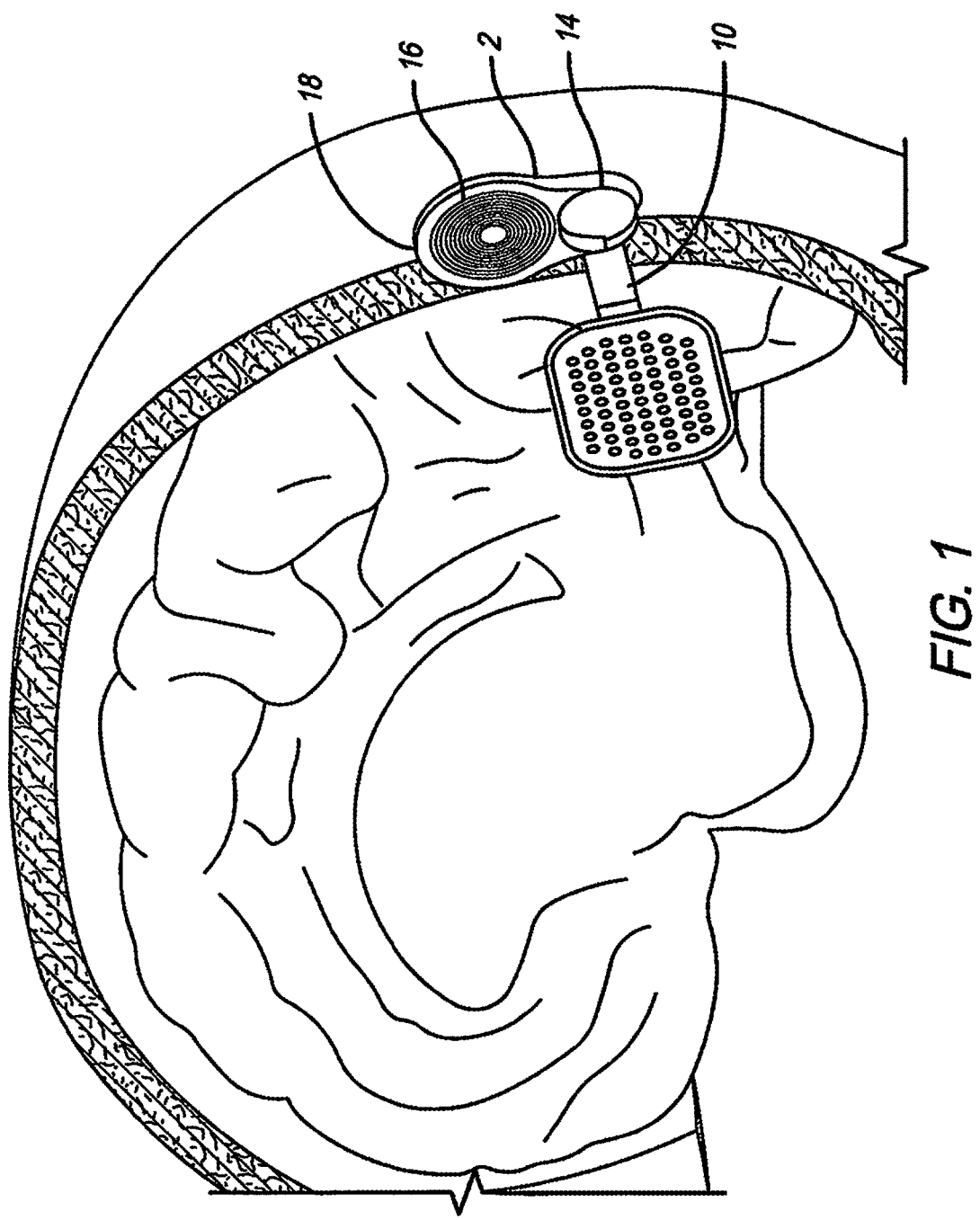

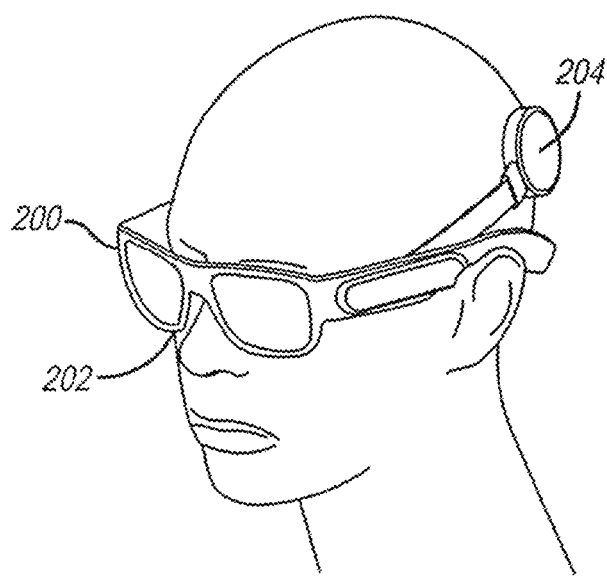
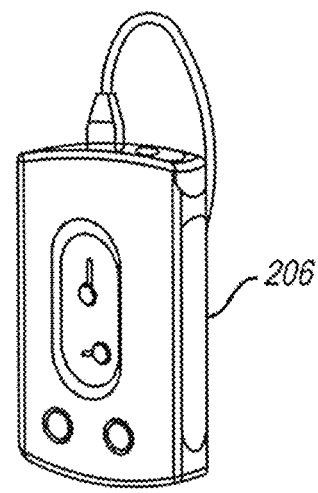
FIG. 24A  FIG. 24B
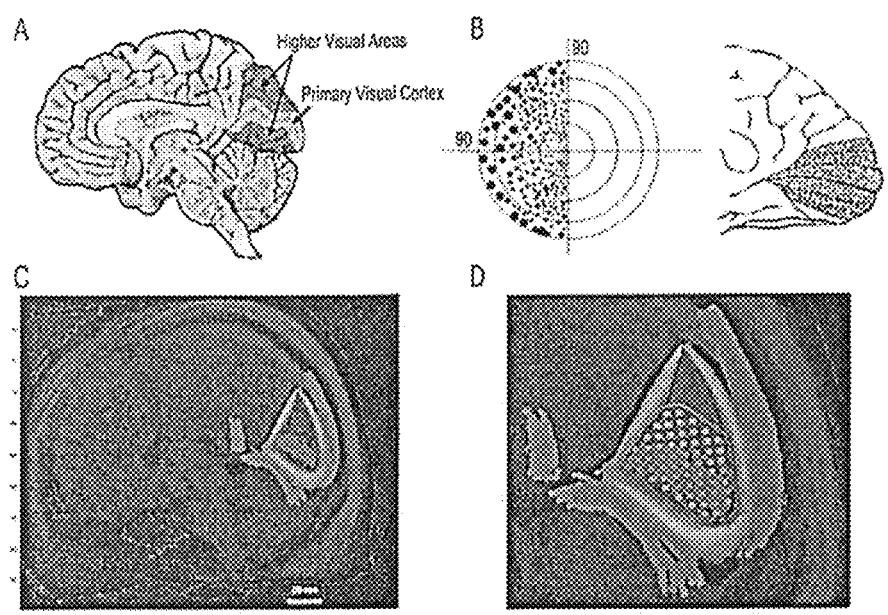
FIG. 25

AGGREGATE ELECTRODE FOR NEURAL STIMULATION

CROSS REFERENCE TO RELATED APPLICATIONS

This application is a divisional application of U.S. patent application Ser. No. 15/154,757 for Cortical Visual Prosthesis, filed May 13, 2016, is now U.S. Pat. No. 9,861,820, which incorporates by reference and claims priority to U.S. Provisional Patent Application 62/161,134 filed May 13, 2015 for Cortical Visual Prosthesis', U.S. Provisional Patent Application 62/170,052 filed Jun. 2, 2015, for Cortical Visual Prosthesis', and U.S. Provisional Patent Application 62/327,944 filed Apr. 26, 2016, for Cortical Visual Prosthesis.

FIELD OF THE INVENTION

The present invention is a flexible circuit electrode array for neural stimulation including an electrode made of multiple smaller electrodes connected by electrical traces.

SUMMARY OF THE INVENTION

The present invention is a flexible circuit electrode array for neural stimulation including a polymer base layer, a metal trace layer on the polymer base layer, and a polymer top layer on the metal traces layer, where the metal trace layer forms at least one electrode made of multiple smaller common electrodes connected by electrical traces.

BRIEF DESCRIPTION OF THE DRAWINGS

FIG. 1 shows the preferred package for the present invention illustrating basic structure and means of attachment and location of implantation.

FIG. 24A is a view of a subject wearing the external portion of the cortical stimulator including glasses with camera and transmitter coil.

FIG. 24B is a perspective view of the video processing unit.

FIG. 25 is an image showing the location of the visual cortex on the brain.

DETAILED DESCRIPTION OF THE PREFERRED EMBODIMENTS

Figure 2A:
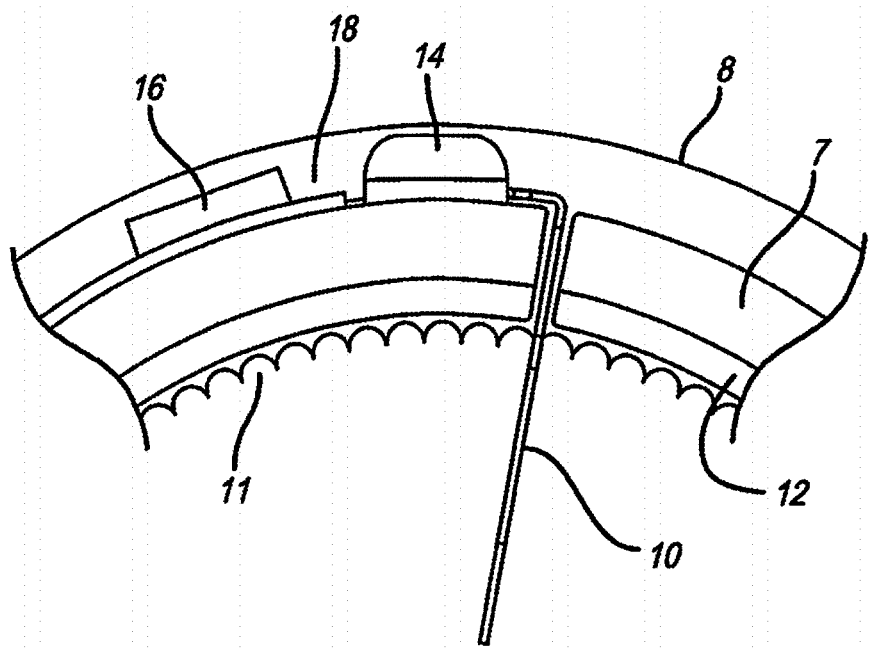
FIG. 2A is a diagram of the invention as implanted for brain penetrating stimulation.

Overall, the present invention has the capability to robustly and reliably stimulate the visual cortex of the brain and be implanted entirely within the head. The preferred embodiment includes a 60 channel stimulator producing a maximum current of 8 mA at a maximum frequency of 120 Hz to 50 kHz. The stimulator produces symmetrical biphasic rectangular pulses with an interphase delay (cathodic or anodic first). The pulse width range is 32 μs to 3.3 ms (0.25 ms at 8 mA). The interphase delay range is 32 μs to 3.3 ms (total waveform<6.6 ms). Electrode diameter: 2 mm. The wireless link range between the implant and external coils is about 30 mm.

Cortical prostheses of the preferred embodiment will provide these features: neural recording, programmable stimulation waveforms, and high current output capability. The electrodes will be coated with platinum gray as described in U.S. Pat. No. 6,974,533, which is incorporated herein, allowing for a chronic charge delivery capability of 1 $mC/cm^2$. The preferred cortical prosthesis will ensure safety though impedance checks, electrode Integrity checks, waveform (pulse & frame) measurements, continuous monitoring of device safety (leakage, overheating, catastrophic failure etc.), and continuous monitoring of device reliability.

The preferred cortical prosthesis will provide research tools for low-level psychophysics experiments. The tools include an extensible programming platform built on top of a psychophysics Application Programming Interface (API). The platform can be used to design and develop low-level psychophysics experiments for subjects (e.g. perception threshold/sensitivity measurements, spatial mapping, dynamic range, two-point discrimination, chronaxie curves, easy and fast creation of optimal configuration parameters, frequency of stimulation, pulse parameters, timing groups and additional configurable systems for testing visual prosthetics.

The preferred embodiment of the present invention is shown in FIG. 1, consisting of an electronics package 14 that is preferably oval or circular in shape (but other shapes are possible), less than 25 mm in diameter (preferably less than 15 mm and more preferably less than 11 mm in diameter), and that is less than 8 mm in height (preferably less than 4 mm and more preferably less than 3.5 mm in height) that is mounted within a hollowed out portion of the cranium or on top of the cranium but under the skin. The package may include a feature for mounting to the cranium such as a low profile flange defining holes to accommodate screws, or tabs that allow screws, sutures or staples to be taken to fix the package (see FIG. 9). Attached to and proceeding from the package 14 is a thin film lead 10 to be routed to the tissue to be stimulated or recorded from. The electrode array is implanted on the surface of the visual cortex. FIG. 1 is a cut away view showing half of the head and brain. The electrode array is suitable to be placed on the cortical surface while the electronics package 14 is within the cranium.

Figure 2B:
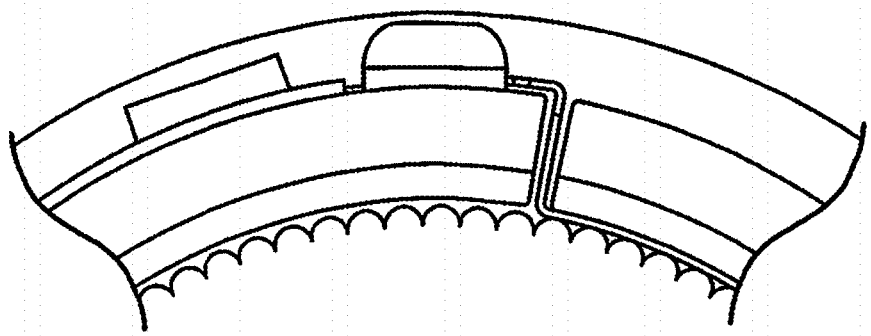
FIG. 2B is a diagram of the invention as implanted for brain surface stimulation.

FIGS. 2A and 2B show attachment of the package 14 to the cranium 7. Alternatively, the package 14 may be affixed to the cranium through the use of one or more straps, or the package 14 may be glued to the cranium using a reversible or non-reversible adhesive attach. In this embodiment, the package, which protrudes from the cranium, is low profile and shaped in manner that permits the scalp 8 to rest on top of the package with little or no irritation of the scalp. Additionally, edges of the package are preferably rounded, and/or the package 14 may be encased in a soft polymer mold such as silicone to further reduce irritation. In other embodiments, the package 14 may be attached to the scalp 8, brain 11, or dura 12. In embodiments with more than one package, each package may be attached to any of the scalp, cranium, dura, or brain.

The improved package of the present invention allows for miniaturization of the package which is particularly useful in brain sensors, stimulators and other prostheses for electrical sensing and stimulation of neural tissue.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by the molded body 18. The molded body 18 holds the electronics package 14 and secondary inductive coil 16 end to end. This is beneficial as it reduces the height the entire device rises above the skull surface. The design of the electronic package (described below), along with a molded body 18 which holds the secondary inductive coil 16 and electronics package 14 in the end to end orientation, minimizes the thickness or height above the skull surface of the entire device.

The Silicone elastomer can be formed in a pre-curved shape to match the curvature of the skull. However, silicone remains flexible enough to accommodate implantation and to adapt to variations in the curvature at a particular site. The implant secondary inductive coil 16, which provides a means of establishing the inductive link between the external processor (see FIG. 24) and the implanted device, preferably consists of gold wire. The wire is insulated with a layer of silicone. The secondary inductive coil 16 may be round or oval shaped. The conductive wires are wound in defined pitches and curvature shapes to satisfy both the functional electrical requirements and the surgical constraints. The secondary inductive coil 16, together with the tuning capacitors in the chip 64, forms a parallel resonant tank that is tuned at the carrier frequency to receive both power and data.

Since the implant device may be implanted just under the scalp it is possible to irritate or even erode through the scalp. Eroding through the scalp leaves the body open to infection. We can do several things to lessen the likelihood of scalp irritation or erosion. First, it is important to keep the overall thickness of the implant to a minimum. Even though it may be advantageous to mount both the electronics package 14 and the secondary inductive coil 16 on the cranium just under the scalp, the electronics package 14 is mounted at a distance laterally displaced from the secondary inductive coil 16. In other words the thickness of the secondary inductive coil 16 and electronics package should not be cumulative.

It is also advantageous to place protective material between the implant device and the scalp. The protective material can be provided as a flap attached to the implant device or a separate piece placed by the surgeon at the time of implantation. Adding material over the device promotes healing and sealing of the wound. Suitable materials include Dacron, Teflon (polytetraflouroethylene or PTFE), Goretex (ePTFE), Tutoplast (sterilized sclera), other processed tissue, Mersilene (Polyester), or silicone.

Figure 3:
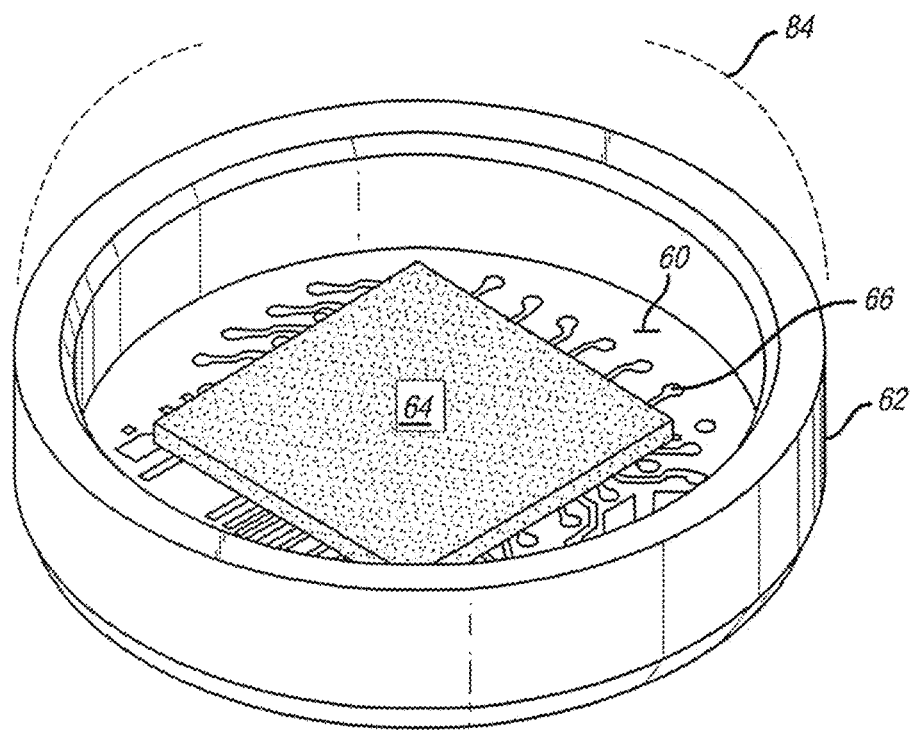
FIG. 3 is a perspective view of a partially built package showing the substrate, chip, and the package wall.

Referring to FIG. 3, the hermetic electronics package 14 is composed of a ceramic substrate 60 brazed to a metal case wall 62 which is enclosed by a laser welded metal lid 84. The metal of the wall 62 and metal lid 84 may be any biocompatible metal such as Titanium, niobium, platinum, iridium, palladium or combinations of such metals. The ceramic substrate is preferably alumina but may include other ceramics such as zirconia. The ceramic substrate 60 includes vias (not shown) made from biocompatible metal and a ceramic binder using thick-film techniques. The biocompatible metal and ceramic binder is preferably platinum flakes in a ceramic paste or frit which is the ceramic used to make the substrate. After the vias have been filled, the substrate 60 is fired and lapped to thickness. The firing process causes the ceramic to vitrify, binding the ceramic of the substrate with the ceramic of the paste forming a hermetic bond.

The package wall 62 is brazed to the ceramic substrate 60 in a vacuum furnace using a biocompatible braze material in the braze joint. Preferably, the braze material is a nickel titanium alloy. The braze temperature is approximately 1000° Celsius. Therefore, the vias and thin film metallization 66 must be selected to withstand this temperature. Also, the electronics must be installed after brazing. The chip 64 is installed inside the package using thermocompression flip-chip technology. The chip is underfilled with epoxy to avoid connection failures due to thermal mismatch or vibration.

Figure 4:
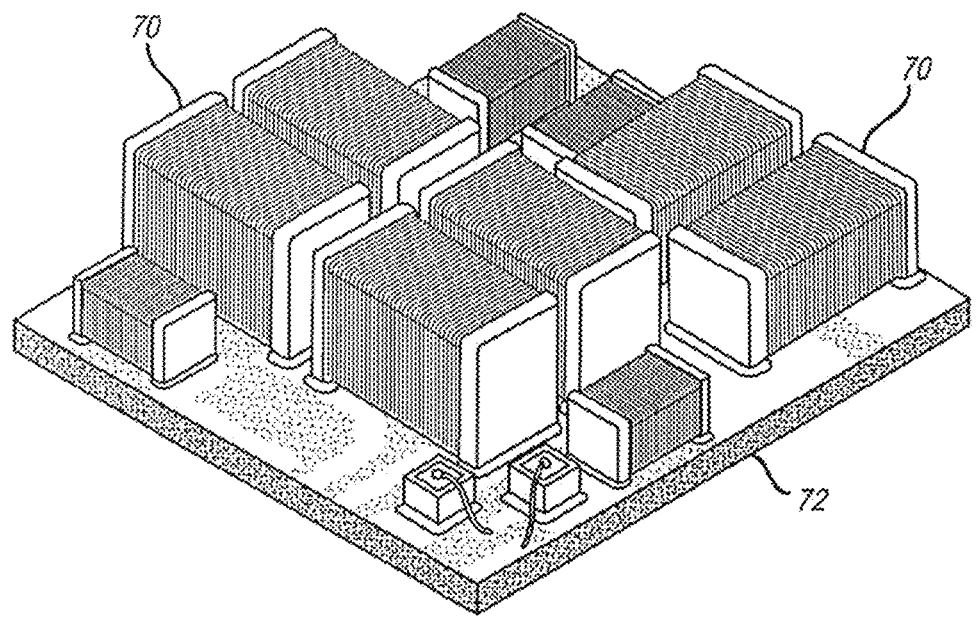
FIG. 4 is a perspective view of the hybrid stack placed on top of the chip.
Figure 5:
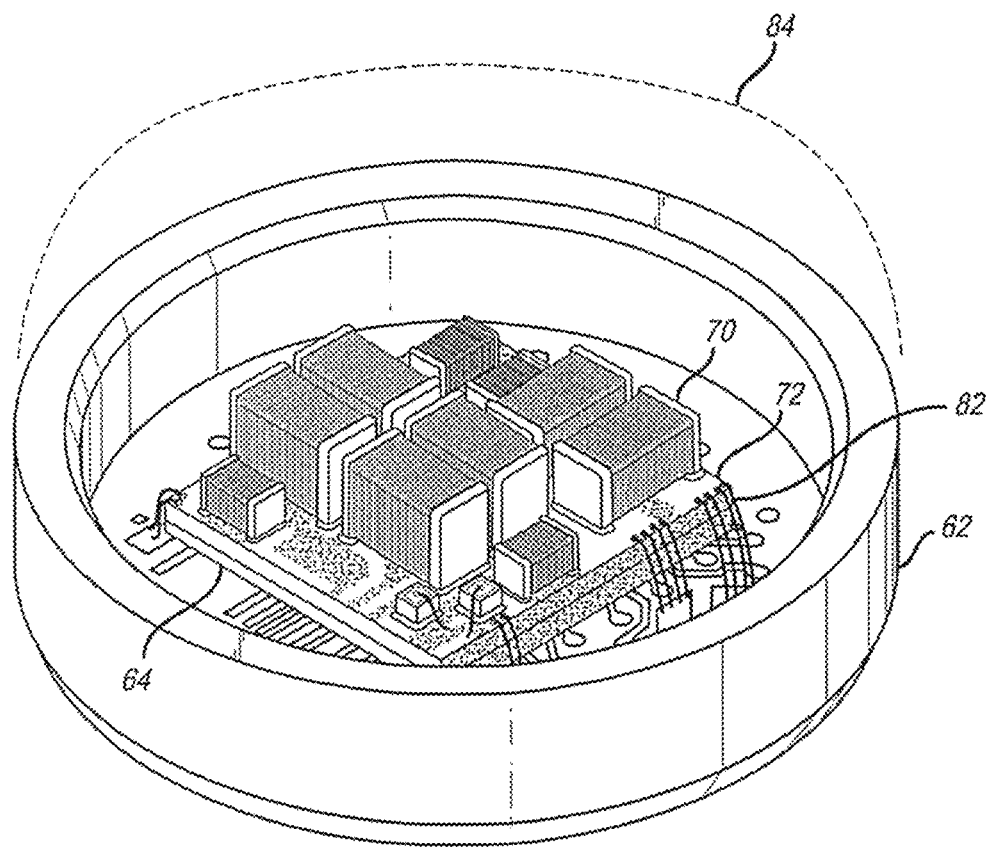
FIG. 5 is a perspective view of the partially built package showing the hybrid stack placed inside.

Referring to FIGS. 4 and 5, off-chip electrical components 70, which may include capacitors, diodes, resistors, or inductors (passives), are installed on a stack substrate 72 attached to the back of the chip 64, and connections between the stack substrate 72 and ceramic substrate 60 are made using gold wire bonds 82. Alternatively, discrete components, or a circuit board, may be attached to the ceramic substrate. A flip-chip integrated circuit and/or hybrid stack is preferred as it minimizes the size of the package 14. The stack substrate 72 is attached to the chip 64 with non-conductive epoxy, and the passives 70 are attached to the stack substrate 72 with conductive epoxy. Thin-film metallization 66 is applied to both the inside and outside surfaces of the ceramic substrate 60 and an ASIC (Application Specific Integrated Circuit) integrated circuit chip 64 is bonded to the thin film metallization on the inside of the ceramic substrate 60.

Figure 6:
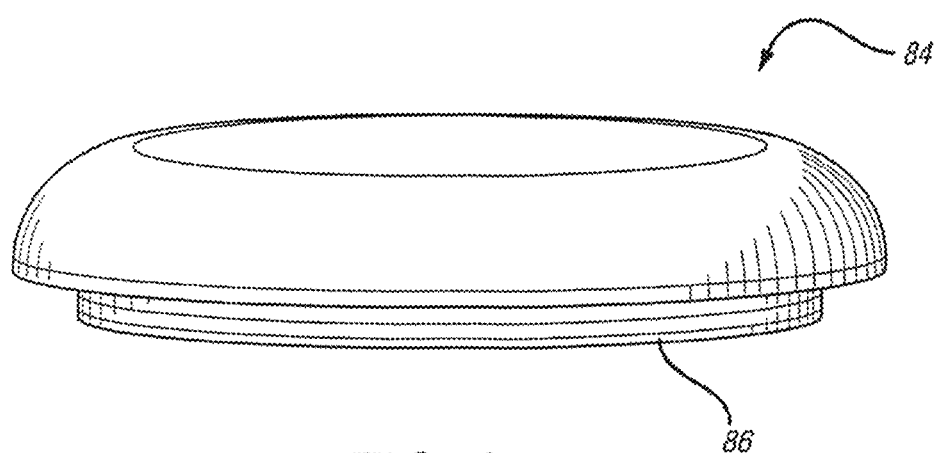
FIG. 6 is a perspective view of the lid to be welded to the top of the package.

Referring to FIG. 6, the electronics package 14 is enclosed by a metal lid 84 that, after a vacuum bake-out to remove volatiles and moisture, is attached using laser welding. A getter (moisture absorbent material) may be added after vacuum bake-out and before laser welding of the metal lid 84. The metal lid 84 further has a metal lip 86 to protect components from the welding process and further ensure a good hermetic seal. The entire package is hermetically encased. Hermeticity of the vias, braze, and the entire package is verified throughout the manufacturing process.

Figure 7:
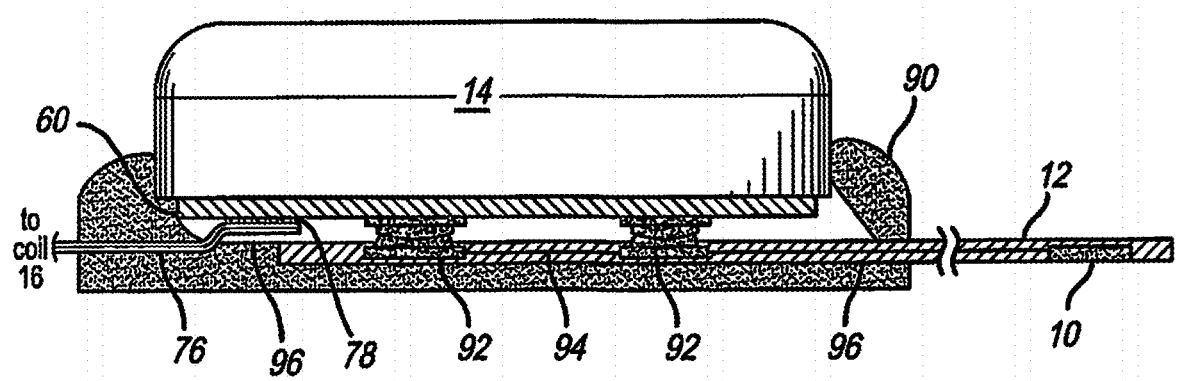
FIG. 7 is a view of the completed package attached to an electrode array.

Referring to FIG. 7, the flexible circuit thin film lead 10 includes platinum conductors 94 insulated from each other and the external environment by a biocompatible dielectric polymer 96, preferably polyimide. One end of the array contains exposed electrode sites that are placed in close proximity to the surface to be stimulated or recorded from. The other end contains bond pads 92 that permit electrical connection to the electronics package 14. The electronic package 14 is attached to the flexible circuit 10 using a flip-chip bumping process, and epoxy underfilled. In the flip-chip bumping process, bumps containing conductive adhesive placed on bond pads 92 and bumps containing conductive adhesive placed on the electronic package 14 are aligned and cured to build a conductive connection between the bond pads 92 and the electronic package 14. Leads 76 for the secondary inductive coil 16 are attached to gold pads 78 on the ceramic substrate 60 using thermal compression bonding, and are then covered in epoxy. The junction of the secondary inductive coil 16, thin film lead 10, and electronic package 14 are encapsulated with a silicone overmold 90 that connects them together mechanically. When assembled, the hermetic electronics package 14 may sit an arbitrary distance away from the end of the secondary inductive coil.

Figure 8:
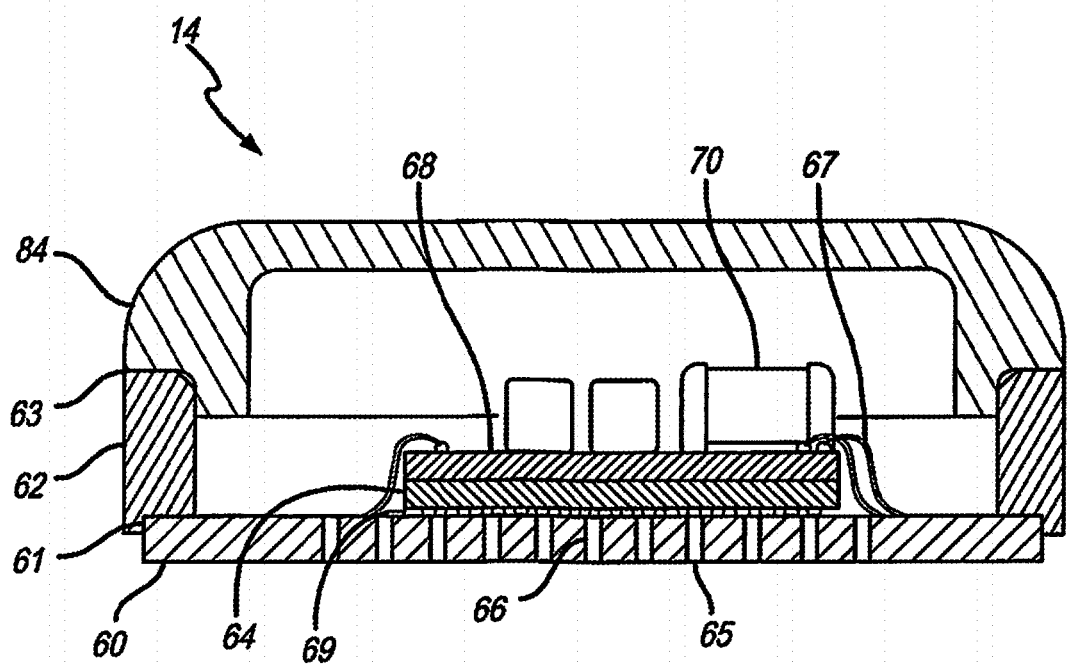
FIG. 8 is a cross-section of the package.

Referring to FIG. 8, the package 14 contains a ceramic substrate 60, with metallized vias 65 and thin-film metallization 66. The package 14 contains a metal case wall 62 which is connected to the ceramic substrate 60 by braze joint 61. On the ceramic substrate 60 an underfill 69 is applied. On the underfill 69 an integrated circuit chip 64 is positioned. On the integrated circuit chip 64, a ceramic hybrid substrate 68 is positioned. On the ceramic hybrid substrate 68, passives 70 are placed. Wirebonds 67 are leading from the ceramic substrate 60 to the ceramic hybrid substrate 68. A metal lid 84 is connected to the metal case wall 62 by laser welded joint 63, whereby the package 14 is sealed.

Figure 9:
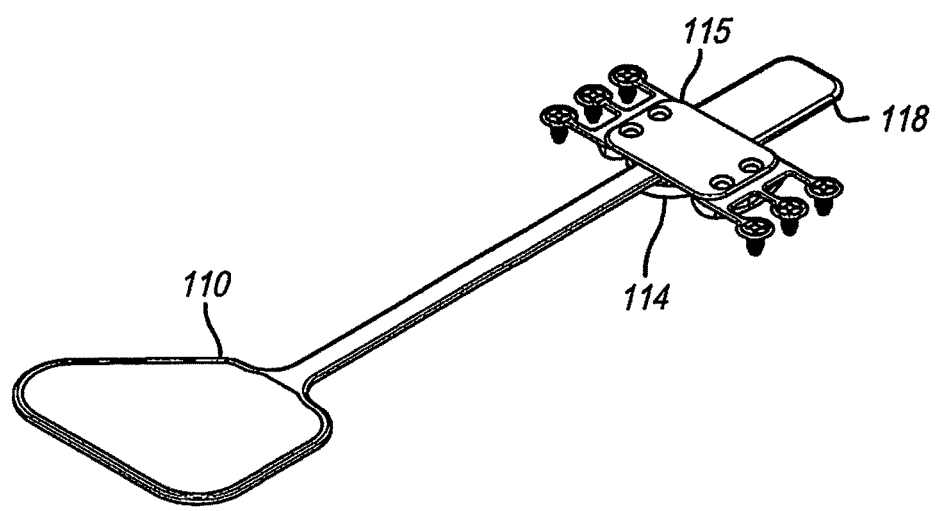
FIG. 9 is a perspective view showing the outside of the implantable portion of the cortical stimulator.
Figure 10:
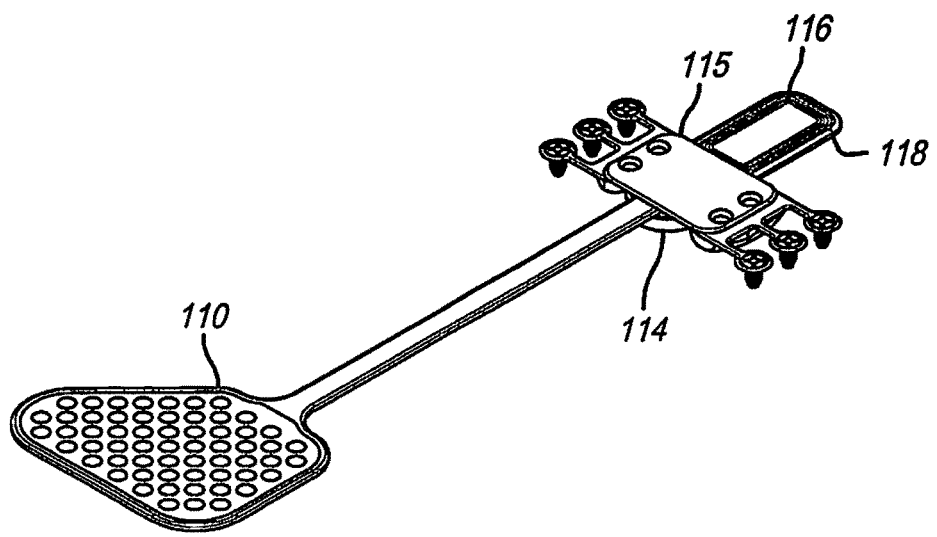
FIG. 10 is a perspective view showing the locations of the electrodes and coil of the implantable portion of the cortical stimulator.

FIG. 9 shows a perspective view of the preferred embodiment showing the outside of the implantable portion. FIG. 10 adds the locations of the electrodes and coil of the implantable portion. Note from this view the electrodes are shown through the flexible circuit electrode array 110. That is, the electrodes are on the other side. It is advantageous that the flexible circuit electrode array 110 be made in a trapezoidal shape with the cable portion attached to the smallest side of the trapezoid. This shape better accommodates the target tissue on the medial surface of the visual cortex. The molded body 119 holding the electronics package 114 and the coil 116 is arranged with the coil 116 opposite the flexible circuit electrode array 110. The device is intended to be implanted with the flexible circuit electrode array 110 attached on top of the package (toward the outside of the skull). This allows the electrodes to be on the same side of the flexible circuit electrode array 110 as the bond pads connecting the flexible circuit electrode array 110 to the electronics package 114, and still face down toward the brain. The ceramic substrate portion of the electronics package 114 to which the flexible circuit electrode array 110 is attached is more delicate than the metal can portion. A mounting fixture 115 covers and protects the electronics package 114, provides screw tabs for attaching the electronics package 114 to the skull, and further provides a heat sink to dissipate heat from the electronics package 114 and a return electrode. The mounting fixture 115 may be any biocompatible metal such as titanium, niobium, platinum, iridium, palladium, or an alloy or combination of such metals. The silicone body 18, described above, may fill, or partially fill, any gaps between the electronics package 114 and the mounting fixture 115. The electronics package 114, coil 116, and molded body 118 are implanted within a hollowed out portion of the skull. It may be necessary to cut through the skull for the electronics package 114, but only part way through the skull for the coil 116, which is not as thick as the electronics package 114. Also, the electronics package 114 can be the return electrode, in which case it needs to contact the dura to reduce impedance. Only a small slot is needed to feed the flexible circuit electrode array 110 through to its implanted location (see FIG. 16). This provides better protection to the brain than an implant where large portions of the skull are removed. The overall device is preferably about 9.7 cm in length. The electrode array portion 110 is preferably about 2.4 cm by 3.4 cm. The coil and electronics molded body is preferably 1.1 cm or less in width. Each electrode is preferably about 2 mm in diameter.

Figure 11:
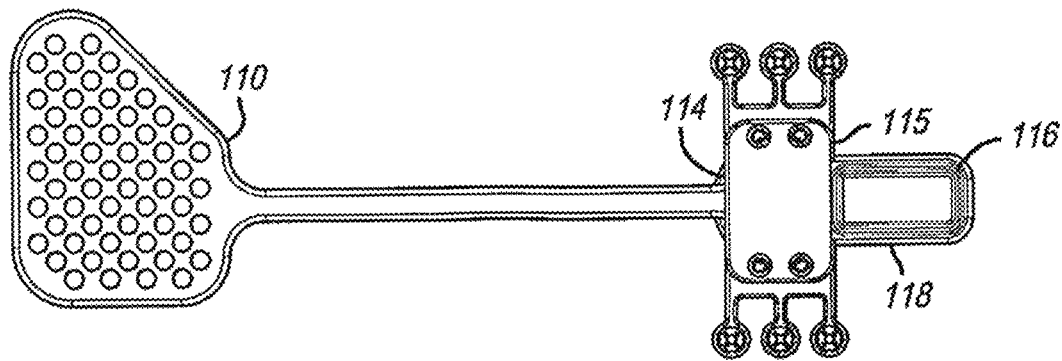
FIG. 11 is a top view of the implantable portion of the cortical stimulator.
Figure 12:
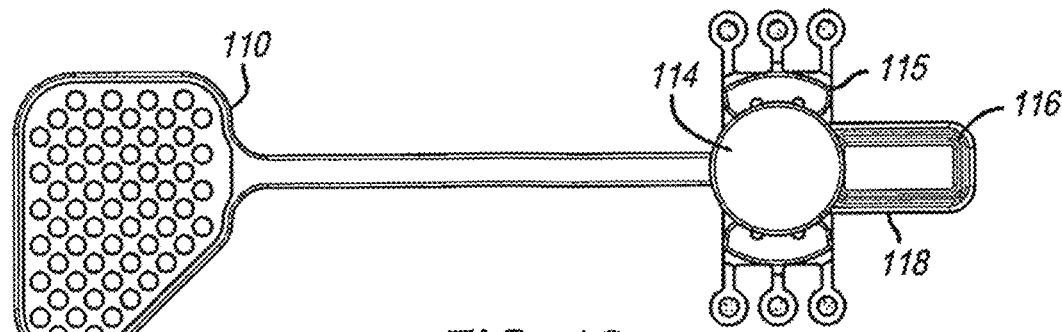
FIG. 12 is a bottom view of the implantable portion of the cortical stimulator.
Figure 13:
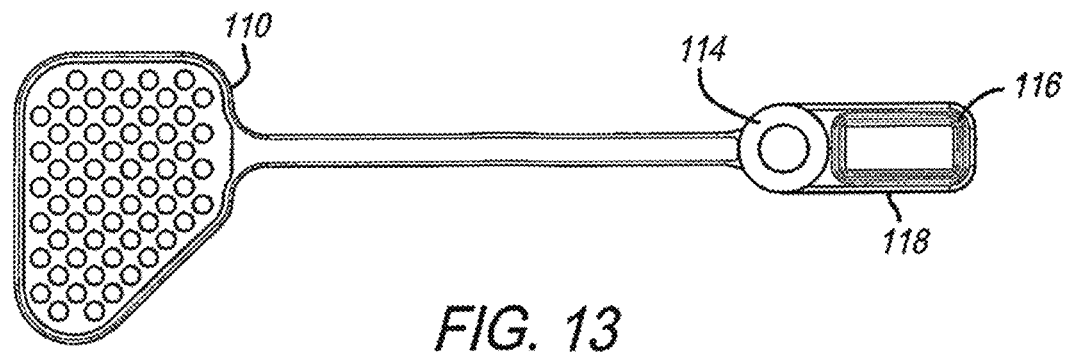
FIG. 13 is a bottom view of the implantable portion of the cortical stimulator excluding the mounting fixture.
Figure 14:
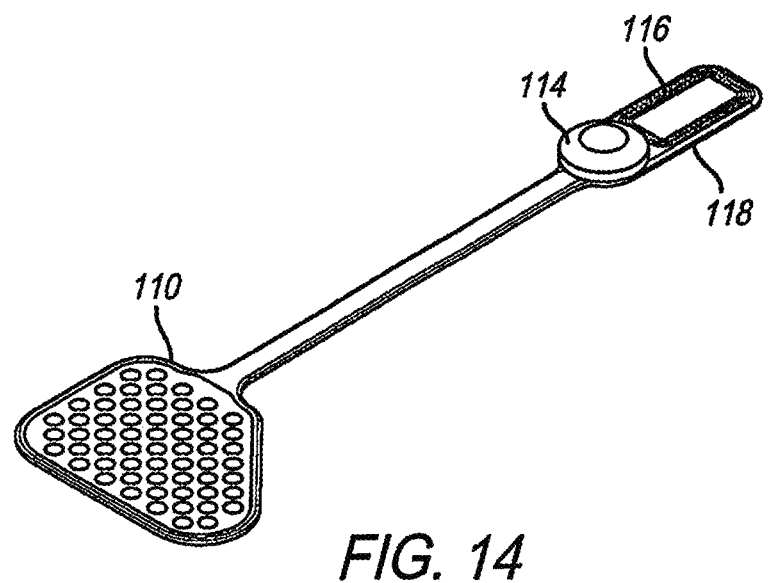
FIG. 14 is a bottom perspective view of the implantable portion of the cortical stimulator excluding the mounting fixture.
Figure 15:
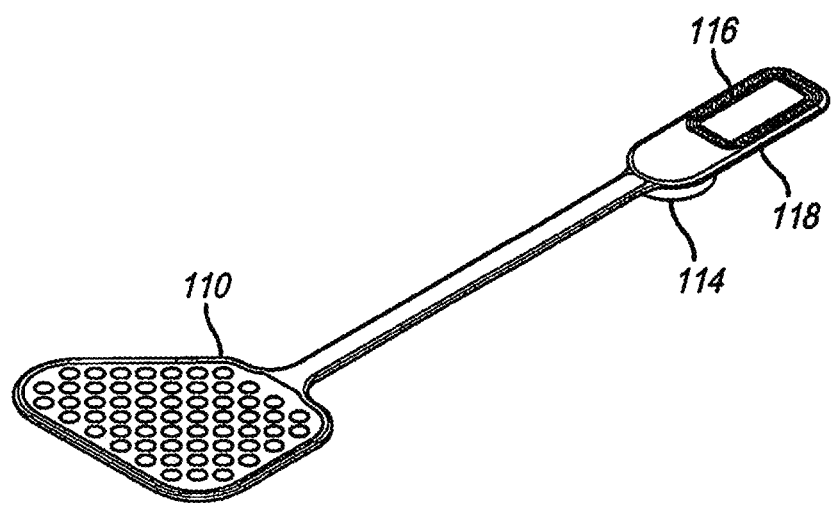
FIG. 15 is a top perspective view of the implantable portion of the cortical stimulator excluding the mounting fixture.

FIG. 11 is a top view of the implantable portion, similar to the perspective views of FIGS. 9 and 10. FIG. 12 provides a bottom view of the implantable portion, opposite of the view previously seen. This is the view that would face the brain when implanted, showing the electrodes. FIG. 13 is a bottom view of the implantable portion excluding the mounting fixture, to better show the electronics package 114. FIG. 14 is a bottom perspective view of the implantable portion excluding the mounting fixture. FIG. 15 is a top perspective view of implantable portion excluding the mounting fixture.

Figure 16:
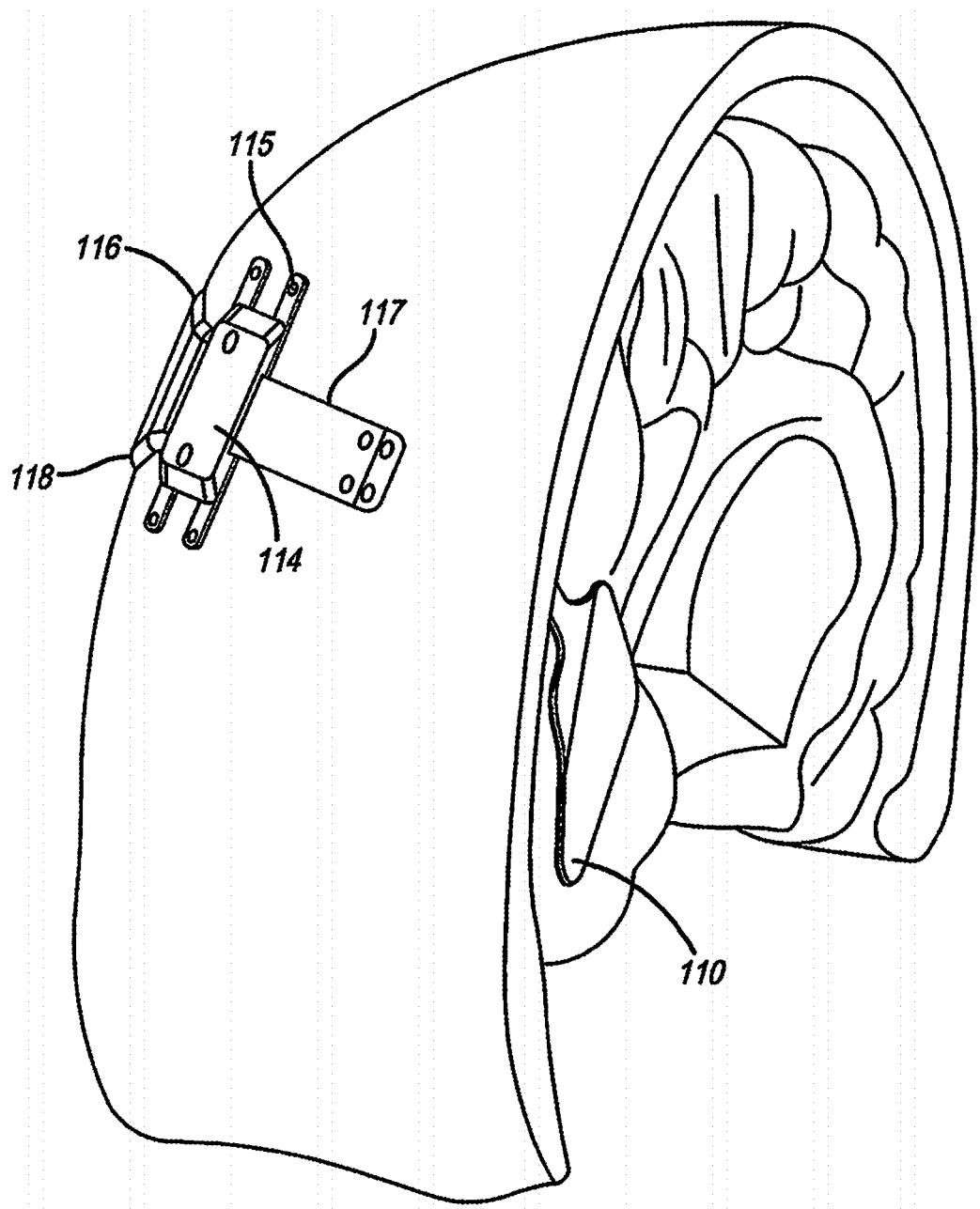
FIG. 16 shows the implantable portion of the cortical stimulator as implanted in a head.

FIG. 16 shows the implantable portion as implanted in a head. The molded body 118, coil 116, and hermetic package 114 are placed in a section of hollowed out skull, preferably not all the way through the skull. Then the fixation structure 115 is screwed into the skull. This protects the hermetic package 114, and prevents any movement of the hermetic package 114 from being transmitted to the flexible circuit electrode array 110 on the brain surface. Only a small slot is required for the flexible circuit electrode array 110 to pass through the skull. In most cases the surgeon will remove a larger area of skull to properly place the flexible circuit electrode array 110. The removed skull is then replaced and the resulting crack is enough to provide for the slot to allow the flexible circuit electrode array to pass through the skull. The rest of the skull may then heal around the flexible circuit electrode array 110.

Figure 17:
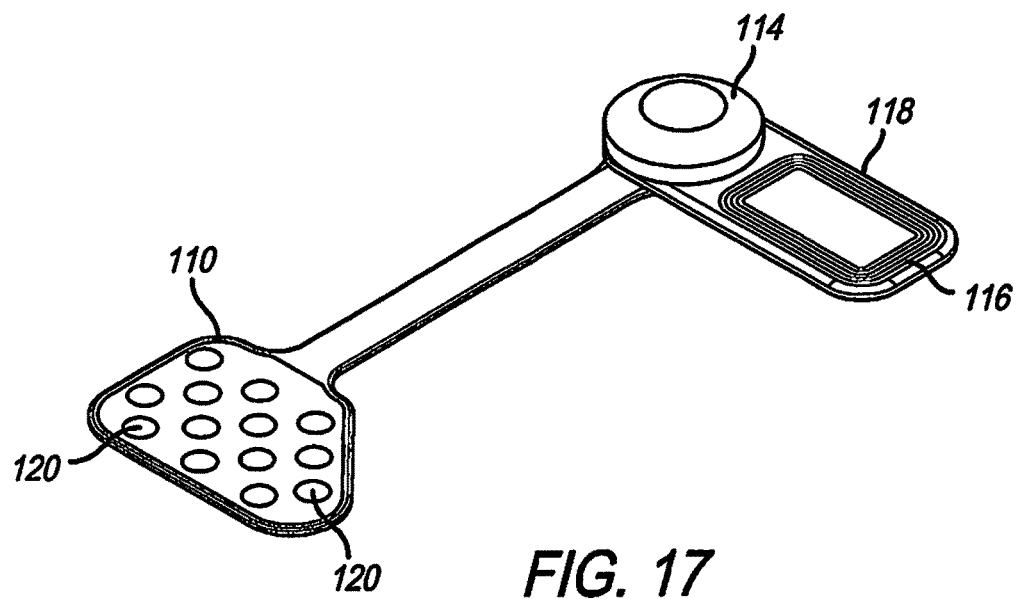
FIG. 17 is a bottom view of a further alternate embodiment.
Figure 18:
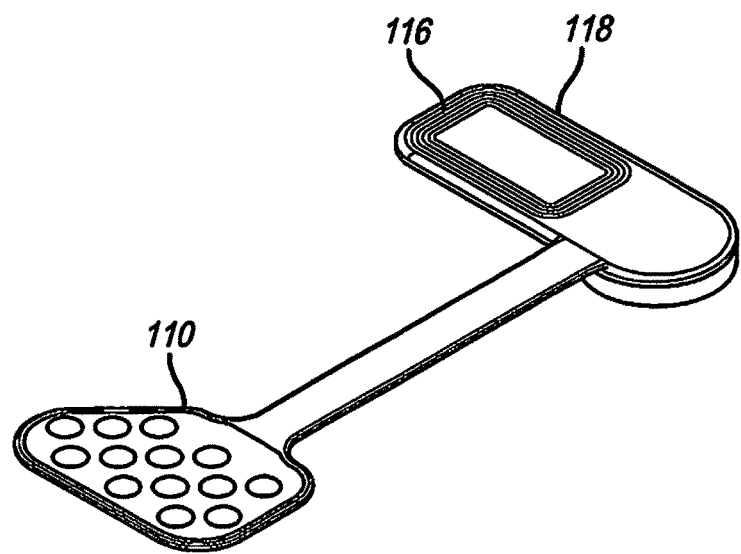
FIG. 18 is a top view of a further alternate embodiment.

FIG. 17 shows a further alternate embodiment as seen from the bottom, or toward the brain. In this embodiment, the coil 116 is at 90 degrees to the flexible circuit electrode array 110. This embodiment may be used on a smaller skull (such as a child or an animal), or where space is otherwise limited. FIG. 18 shows the alternate embodiment of FIG. 17 from the top, or away from the brain.

Figure 19:
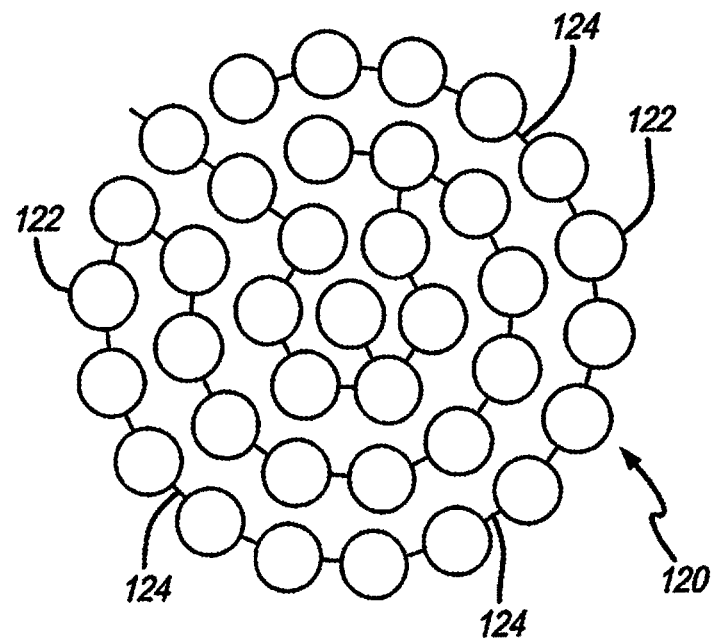
FIG. 19 is an aggregate electrode according to the present invention.

Referring to FIG. 19, the electrodes shown in FIGS. 10-15, 17, and 18 are aggregate electrodes 120 within the electrode array 110, not single electrodes. Aggregate electrodes 120 are made up of small sub-electrodes 122. The small sub-electrodes 122 are linked by traces 124 to make the sub-electrodes 122 common, and forming an aggregate electrode 120. In order to stimulate neurons relatively far from the electrode surface (over 1 mm), such as in subdural cortical applications, the aggregate electrode 120 diameter needs to be of a similar size. Conventional electrodes are a circle, filled entirely of the electrode material. Creating a large thin-film electrode in that manner is prone to problems of manufacturability and long-term reliability, and plating deposits may flake off.

The deposition of the platinum gray or other advanced materials over such a large area introduces stresses into the material that may lead to cracking or delamination. The adhesion of the metal to the underlying polymer will also be poor, creating a high risk of delamination of the layers.

In this design, the outer diameter of the aggregate electrode 120 is large (between 1 and 3 mm), but the surface area of electrode material is reduced. This is achieved through distributing the electrode material as discrete islands or sub-electrodes 122. The sub-electrodes are shorted together through platinum traces 124 embedded in the underlying polymer dielectric. The diameter of each sub-electrode 122 is 200 um, equivalent to the existing electrode diameters, a size in which platinum gray is deposited without creating excessive stress in the material. The stability and reliability of sub-electrodes 122 of this size has been demonstrated in lab testing and long-term implantation. The amount of metal conductor is also minimized in this design, providing a larger area for strong polymer interface bonding. While the sub-electrodes are normally relatively flat, in an alternate embodiment the sub-electrodes are made to protrude somewhat from the electrode array surface, into the cortical tissue to help reduce thresholds. In another alternate embodiment, the entire group of sub-electrodes that form an aggregate electrode are protruding slightly together as a group into the cortical tissue; in this case the electrode array surface between and around the sub-electrodes is slightly raised in a gentle, mound-like configuration.

Figure 20:
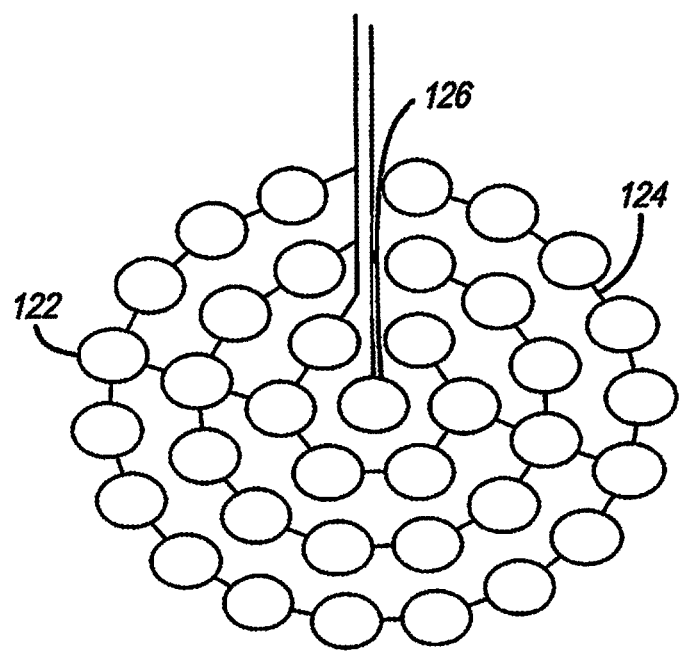
FIG. 20 is an aggregate electrode with a center sensing electrode.

Current density is non-uniform over an electrode, and is highest at the edges, termed the 'edge effect'. This is typically not desirable as the high current density has greater potential for damage to the electrode and/or target neurons. This design significantly increases the total perimeter length of the electrode 120, offering the opportunity for a more uniform current distribution. The current density distribution can be further optimized through customized routing and width of the platinum conductor traces such that center electrodes experience higher current flow than the edge electrodes Referring to FIG. 20, another potential configuration is to use one or more of the electrodes 126 as a sensing electrode, wired separately from the rest of the sub-electrodes 122. This would allow for optimization of the sensing electrode diameter, and enable sensing of tissue response before, during and immediately after stimulation.

Figure 21:
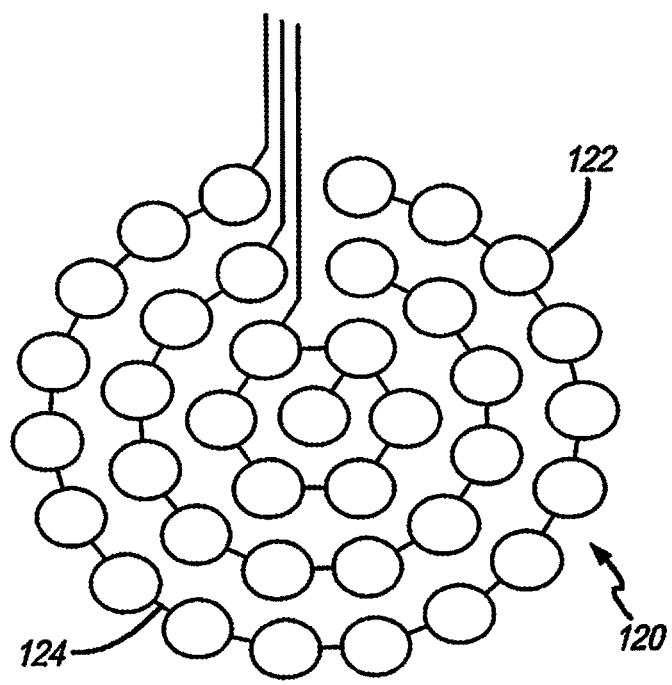
FIG. 21 is an aggregate electrode with variable size segments.

Referring to FIG. 21, a further configuration is to wire one or more rings of sub-electrodes 122 independently from the others. The aggregate electrode 120 diameter can therefore be changed through software, where all rings can be pulsed together to act as a large aggregate electrode 120, or by disabling outer rings, could behave as a smaller aggregate electrode 120. This could be done as a part of patient fitting in the clinic, or real-time, to allow for dynamic percept size.

Figure 22:
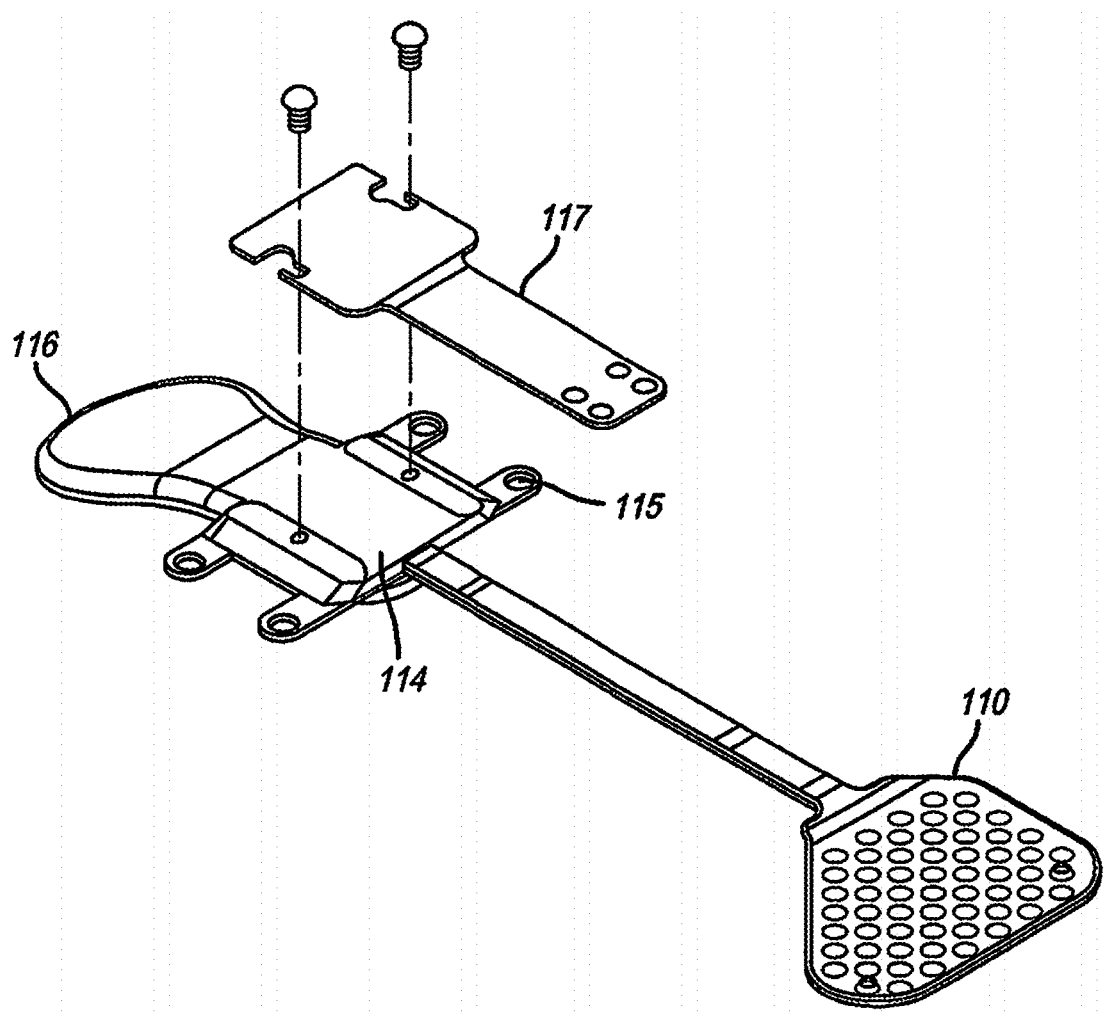
FIG. 22 is a perspective view of the implant components including a protective cover plate.

Referring to FIG. 22, the implant may also include a cover plate 117. The cover plate protects the implant in the cases of a blow to the head. The cover plate 117 may be any biocompatible metal such as titanium, niobium, platinum, iridium, palladium, or an alloy or combination of such metals. The cover plate 117 may also serve as part of the return electrode. The implant consists of: an electrode array 110 and cable; a secondary coil 116 for receiving information and power from the external components; hermetically-encased electronics 114 to drive stimulation of the electrodes; and a cranial socket 115 and cover plate 117.

Initial array dimensions have been determined from published data on functional mapping of the visual cortex. The array will be of similar size to those used by Brindley and Dobelle, so similar visual field extents of 20° to 30° are expected; this is similar to the Argus II visual field (about 20°). The initial array dimensions are sized to fit within the bounds of the visual cortex, at 34 mm long and 24 mm tall in a trapezoidal configuration (as shown in FIGS. 9-15 and 22). Placement of the array may be guided by anatomical landmarks and pre-operative MRI. Visual cortex location is fairly consistent, and anatomical landmarks have been shown to be predictive of visual field mapping, so consistent placement in visual areas is not expected to present any significant difficulty. If necessary, fluoroscopy can be used to assist in placement as the electrode array contains two radio-opaque markers near its extremities.

Various electrode sizes may be employed in a layout such as a checkerboard where every alternate electrode is of a smaller size. This approach was used in several of the first generation Argus implants to gather data on the quality of the percepts with respect to electrode size. The electrodes will be up to 2 mm in diameter, which have been reported to produce punctate phosphenes generally indistinguishable from smaller electrodes while also encompassing enough surface area to allow for safe charge densities.

The aggregate electrodes are square, packed with 3 mm center to center distance, a sufficient spacing which should allow for distinct percepts. Sixty electrodes will be used initially so that the existing mature Argus II electronics can be leveraged in this design. The only minor change to the implantable electronics is to supply more current (8 mA vs 1 mA in Argus II), which, based on the literature, should be adequate for surface cortical stimulation, and furthermore, is still within the safe charge limits described by Shannon and McCreary for these relatively large aggregate electrodes.

Direct anchoring to the brain tissue will not be necessary for the electrode array, since this is the current practice with subacute and chronic implantation of subdural electrocorticographic arrays for epilepsy monitoring, and responsive neurostimulation, respectively. The design of the novel flexible electrode array will incorporate an elongated, integrated, flexible polymer cable to accommodate movement of the brain relative to the dura and skull. To avoid damage to tissue from sharp polymer edges, the array and cable will be given a soft silicone bumper around the edge, as in the Argus II System.

Figure 23:
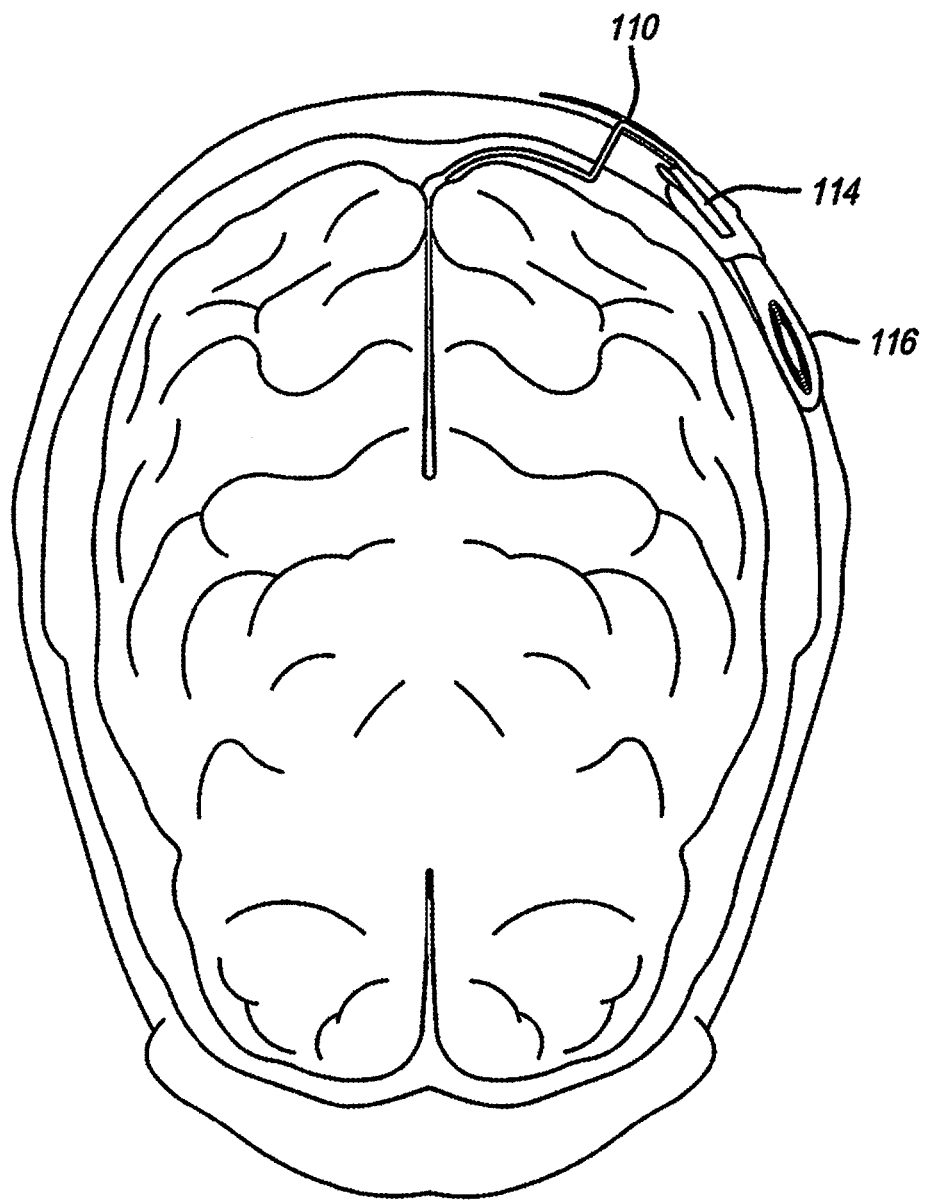
FIG. 23 is a top view of a skull showing the location of the implantable portion of the cortical stimulator.

Referring to FIG. 23, the placement of the internal coil and electronics case is another key aspect of the design. The electronics for the cortical prostheses will be affixed to the skull. This is similar to the placement used for the NeuroPace closed loop stimulator for epilepsy, and the first generation of the Argus implant. The electronics package will be embedded inside a metal cranial socket. The cranial socket serves a multifold role of protecting the implant, providing anchor points to the skull, assisting in dissipating heat generated by the electronics, and providing a large surface area return electrode for the stimulating current.

Referring to FIGS. 24A and 24B, the external components are an absolutely critical part of the system. They are based on those of the Argus II System (now in its 16th revision), with modifications for the cortical stimulation. As in the Argus II, the main components will be the Glasses 200 and a Video Processing Unit (VPU) 206. A small, lightweight video camera 202 will be mounted on the glasses. The telemetry coils 204 and radio-frequency system for transmitting data from the VPU 206 to the implant will be positioned so they rest on the back of the head, in close apposition to the implanted coil 116.

The VPU 206, which is worn on a belt or strap, is used to process the images from the video camera 202 and convert the images into electrical stimulation commands; these are transmitted wirelessly to the implant.

Referring to FIG. 25, the visual cortex is composed of the striate cortex (V1) and extrastriate areas (V2, V3 and higher visual areas), which all have some exposure on the medial surface of the occipital lobe. V1 is the primary visual cortex, and is the first step in cortical processing of visual signals. Like the retina, physical locations in V1 are mapped to locations in visual space (retinotopic or visuotopic mapping). V1 starts at the posterior pole of the occipital lobe and follows the calcarine sulcus anterior along the medial surface of the brain. On average, 4.6 $cm^2$ of V1, 22% of its total surface area is exposed on the medial surface, while the majority is buried in the calcarine sulcus. The electrode area of the implant will be approximately 6.5 $cm^2$, larger than the exposed V1 area, so some electrodes will stimulate extrastriate areas V2 and V3. These two areas surround V1 and each have visuotopic mapping to the entire visual field, which allows for the implant to stimulate parts of the field that for V1 are buried in the calcarine sulcus. Encouragingly, stimulation of V2 and V3 has been shown to produce single distinct phosphenes, similar to that observed with stimulation of V1.

The extent of visual field is known to be one of the most important factors in visually-guided mobility. The best way to cover a large part of the visual field with an electrode array is to locate electrodes over a wide area on the medial surface of the visual cortex. The medial surface can access all but the very central two to three degrees of visual field.

The upper and lower visual fields are split by the calcarine sulcus, with the upper visual field located below the sulcus, and the lower field above the sulcus (FIG. 25C). The electrode array will span both sides of the sulcus, to cover upper and lower vision. A single electrode array will stimulate one hemisphere, which activates the visual field on the contralateral side. Initially, one can implant a single array, so one half of the visual field (left or right) will be stimulated. However, cortical visual prosthesis can enable bilateral implants and stimulation. This can be accomplished with a single driver and two arrays, or two independent implants with driver and array.

During testing sessions, a subject's Video Processing Unit can be wirelessly connected to a laptop or tablet device. Downloadable apps are used to perform psychophysics research—to determine how stimulation parameters affect the appearance and location of phosphenes. The apps allow the subjects' VPUs to be custom-programmed for stand-alone camera use (i.e., with the electrode stimulation pattern being derived from the video feed). We have leveraged and built on the Argus II programming and testing software (currently in its 16th revision).

The measured impedances of the electrodes range between 1 k-2.5 k ohms. Some variation is observed in the first few weeks post implantation before the impedance values stabilize. This variation is typical and believed to be caused during the body's normal response to a foreign body.

A few iterations of mechanical (non-functional) models of the implant have been designed, manufactured, and tested in the nonclinical setting. Several initial prototypes of the array and implant were used in cadaver dissections to identify possible surgical approaches and to evaluate the array size and thickness, cable length, and flexibility of materials needed for safe implantation.

Figure 26:
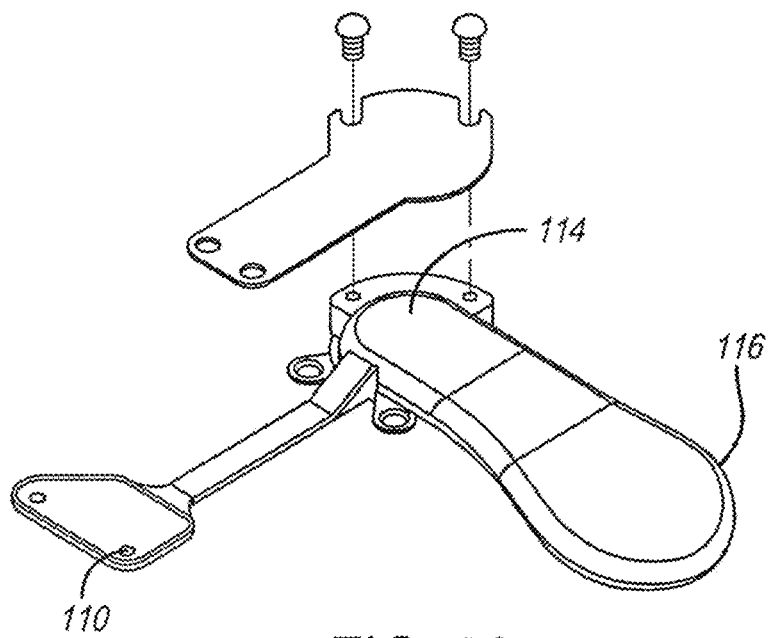
FIG. 26 is a view of a child or animal version of the implant.
Figure 27:
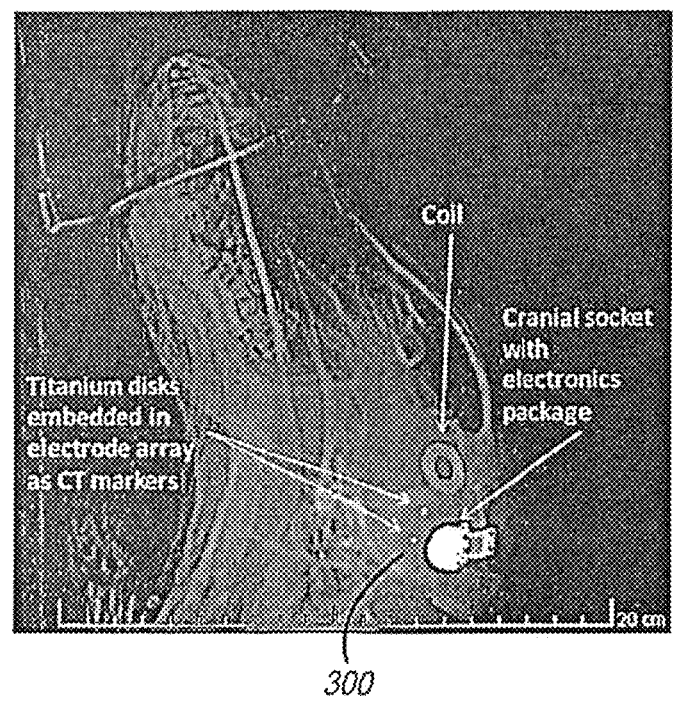
FIG. 27 is an x-ray showing the animal version as implanted.

In addition, both mechanical models and working prototypes of the full implant, including array, cable, implant coil, electronics package, and cranial socket were built for testing in animals (see FIG. 26). The implant coil and electronics case were replicas of those for use on humans while the array size was reduced to fit the smaller brain, with a corresponding reduction in number of electrodes. To date, five mechanical models and six fully functional prototypes have been implanted in the animals (FIG. 27). Metallic markers 300, preferably titanium, may be added to the electrode array to assist in locating the array in an X-ray or CT scan. The stimulating electrodes were placed on the left hemisphere of the medial occipital cortex. The primary goals of the animal studies were:

1. Assess suitability and safety of the implant procedure, via surgeon feedback and collection of intraoperative adverse events.
2. Assess the long-term safety of the implant, via collection of adverse events during the follow-up period.
3. Assess the biocompatibility of the implant, via analysis of gross and microhistology.
4. Demonstrate the long-term functionality of the implant, via collection of impedance and implant diagnostic measurements throughout the study.
5. Evaluate the implant for electrode array migration, via CT scan.
6. Demonstrate compliance of the implant to international standards with respect to in-vivo temperature rise of the implant during activation.
7. Demonstrate ease of explant and effect of explant surgery on the animal model.
8. Demonstrate the safety of chronic stimulation on neural tissue.

During the course of animal studies conducted thus far, the implant design was refined iteratively to improve its performance with respect to the above criteria. The performance of these devices was monitored regularly by measuring the impedance. The devices were also used to apply electrical stimulation to the visual cortex of the animals. While applying stimulation current, the animals are sedated so the external coil can be positioned properly for continuous communication. Under mild sedation it was noted that the animals tended to consistently turn their heads to the right as soon as stimulation current was applied (as if looking at something). While it cannot be conclusively stated that they were experiencing visual percepts, the direction of turning was always to the right, which would be consistent with the field of visual percepts produced by stimulation of the left visual cortex.

The measured impedances of the electrodes range between 1 k-2.5 k ohms. Some variation is observed in the first few weeks post implantation before the impedance values stabilize. This variation is typical and believed to be caused during the body's normal response to a foreign body. Following long-term (several months) implant, the animal is sacrificed and histopathology is performed. To date, the histopathology has not shown any significant levels of tissue reaction or neuropil. Expected fibrous encapsulation of the device is observed to varying degrees, both on the skull mounted electronics package, and the flexible electrode array. No physiological or behavioral changes were observed in the animals post-implantation or post-explanation.

Accordingly, what has been shown is an improved cortical visual prosthetic for implantation in a body. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What we claim is:

1. A flexible circuit electrode array for neural stimulation comprising:
    a flexible polymer base layer;
    a flexible metal trace layer on the polymer base layer; and
    a flexible polymer top layer on the metal trace layer;
    wherein the metal trace layer forms at least one flexible aggregate electrode, having a first diameter, made of multiple smaller sub-electrodes shorted together by electrical traces to make the sub-electrodes common, and each sub-electrode is within the first diameter and having a second diameter smaller than the first diameter.

2. The flexible circuit electrode array according to claim 1, further comprising multiple aggregate electrodes forming an electrode field.

3. The flexible circuit electrode array according to claim 2, wherein the electrode field forms a trapezoidal shape.

4. The flexible circuit electrode array according to claim 1, further comprising at least one electrode surrounded by the sub-electrodes, which is not common to the sub-electrodes.

5. The flexible circuit electrode array according to claim 4, wherein the at least one electrode is a sensing electrode.

6. The flexible circuit electrode array according to claim 1, further comprising groups of sub-electrodes that are separately controllable.

7. The flexible circuit electrode array according to claim 6, wherein the groups of sub-electrodes are rings of sub-electrodes.

8. The flexible circuit electrode array according to claim 1, wherein the sub-electrodes protrude slightly from the surface of the flexible circuit electrode array and are configured to protrude into cortical tissue.

9. The flexible circuit electrode array according to claim 1, wherein the first diameter of the aggregate electrode is between 1 and 3 mm.

10. The flexible circuit electrode array according to claim 1, wherein the second diameter of each sub-electrode is about 200 µm.

11. The flexible circuit electrode array according to claim 1, wherein the aggregate electrode is protruding.

12. The flexible circuit electrode array according to claim 1, further comprising a surface coating deposited on each sub-electrode.

13. The flexible circuit electrode array according to claim 12, wherein the surface coating is platinum grey.

* * * * *